United States Patent [19]

Kay et al.

[11] Patent Number: 4,839,298

[45] Date of Patent: Jun. 13, 1989

[54] VIRUS INACTIVATING DILUENTS USED IN IMMUNOASSAYS

[75] Inventors: John W. D. Kay; Glen M. Ford, both of Raleigh, N.C.

[73] Assignee: Akzo N.V., Arnhem, Netherlands

[21] Appl. No.: 68,283

[22] Filed: Jun. 30, 1987

Related U.S. Application Data

[63] Continuation of Ser. No. 830,670, Feb. 14, 1986, abandoned, Continuation-in-part of Ser. No. 788,735, Oct. 17, 1985, abandoned.

[51] Int. Cl.$^4$ .............................................. G01N 1/00
[52] U.S. Cl. .................................... 436/175; 436/174; 436/176; 436/820; 436/22; 436/536; 424/89; 424/101; 435/5; 435/7; 435/238
[58] Field of Search ............... 424/89, 101; 435/5, 435/238; 436/820, 175, 176

[56] References Cited

U.S. PATENT DOCUMENTS

| 4,314,997 | 2/1982 | Shanbrom | 424/101 |
| 4,613,501 | 9/1986 | Horowitz | 435/238 |
| 4,619,896 | 10/1986 | Shattock et al. | 435/7 |
| 4,645,666 | 2/1987 | Manning et al. | 435/238 |

*Primary Examiner*—Sam Rosen
*Attorney, Agent, or Firm*—William M. Blackstone

[57] ABSTRACT

Diluent compositions for preparing specimens for immunoassay contain effective amounts of salt and non-ionic surfactants to inactivate viruses in the specimens and improve the sensitivity and specificity of the immunoassays; said diluents having some strengths of from about 21 to about 35 mS/cm and comprising 0.05 to 1% non-ionic surfactants, along with other conventional ingredients. The invention relates as well to immunoassay procedures using the novel diluents.

19 Claims, 3 Drawing Sheets

FIG. 1

INACTIVATION OF HTLV-III BY NON-IONIC SURFACTANT

VIRUS INACTIVATING DILUENTS USED IN IMMUNOASSAYS

This application is a continuation application of U.S. patent application Ser. No. 06/830,670, filed Feb. 14, 1986, which is a continuation-in-part application of U.S. patent application Ser. No. 06/788,735, filed Oct. 17th, 1985, both now abandoned.

BACKGROUND OF THE INVENTION

This invention relates to compositions for inactivating viruses that can be used as diluents for preparing immunoassay specimens. These inactivating compositions have the additional advantageous characteristics of improving both the selectivity and sensitivity of tests based on the antibody-antigen reactivity of the viruses.

Enzyme-linked immunosorbent assays (ELISA) are well-known immunoassays that provide a routine means for detecting antibodies to specific antigenic determinants, including those found on viruses, which are particularly useful in screening large numbers of samples. In these tests an antigen is immobilized on a solid support, and specimens that may contain the respective antibody are placed in contact with the immobilized antigens. Any unobstructed antibodies that are present in the specimens become bound to the fixed antigens. As the bound antibodies contain immunoglobulin characteristic of their source, e.g., human serum antibodies contain human immunoglobulin, the bound antibody is detected by contacting the solid phase medium with "anti-source" immunoglobulins, e.g., anti-human immunoglobulins, that are linked to a detectable tag, such as an isotope or an enzyme. After contacting the solid phase with a specimen and washing the solid phase, the detection of the tag on any solid phase sample indicates the presence of the antibody. The same principles apply in immunoassays that immobilize antibodies in the solid phase and detect antigens present in test specimens.

Immunoassay tests, being highly sensitive, are conducted using diluted specimens. Dilution aids in eliminating or reducing interference that may be caused by other components of the specimen. Commonly used diluents comprise water, serum, buffered saline and preservatives and do not inactivate pathogenic organisms or viruses. As a result, substantial quantities of diluted specimens, wash solutions and solid substrates are produced during the course of conducting ELISA and other immunoassay tests, the handling and disposal of which becomes a significant problem as large quantities of waste liquids are produced that could contain infectious agents. For example, in large-scale assays of blood and blood products for viruses such as Human T-Lymphotropic Virus Type III (HTLV-III) and Hepatitis virus, the tested specimens, the waste solutions and the used solid media could be sources of infection for laboratory workers and others. Accordingly, a means for inactivating any pathogenic virus that may be in the specimens tested is of great importance for eliminating a significant health hazard.

The inactivation of HTLV-III with reagents and methods commonly used in virology laboratories have been studied by several investigators. Spire et al reported the inactivation of HTLV-III with sodium hypochlorite, $\beta$-propionolactone, formalin, glutaraldehyde, formalin and ethanol by incubating the virus with various concentrations of each disinfectant for one hour and assessing inactivation by analyzing for reverse transcriptase activity (*The Lancet*, Oct. 20th, 1984). Spire et al, in a different article, reported the results of inactivation tests using heat, gamma radiation and ultraviolet radiation (*The Lancet*, Jan. 26th, 1985), in which inactivation was only achieved at relatively high temperatures and radiation levels. Martin et al also reported inactivation using conventional laboratory disinfectants and detergents (*The Journal of Infectious Diseases*, Volume 152, No. 2, August 1985). All of the chemical agents tested by these investigators caused inactivation at certain concentrations, except for Tween-20 TM detergent. With the exception of the Tween-20 TM and Nonidet P-40 detergents, all of the chemical agents reviewed by these investigators were known to be strong disinfectants. It was reported that Nonidet P-40 (NP-40) provided adequate inactivation at a concentration of 1.0 weight percent. Tween-20 TM, however, did not prove to be an effective inactivating agent, even at concentrations as high as 2.5%.

In virology laboratories it is common to use high concentrations of detergents and salt together for inactivating viruses, as detergents are known to remove the protein envelope and the salt causes the nucleotide-protein core to dissociate. Such media have not been used as diluents for preparing specimens of, for example, serum, blood, plasma or urine, however, because concentrations of detergents and salt sufficient to render a virus inactive would have been expected to interfere with the analytical results. For example, NaCl is known to precipitate ribonucleic acids. Moreover, antigen-antibody reactions are ionic and high concentrations of salt would theoretically affect the surface charges on the antigen and antibody molecules, thus interfering with the formation and stability of the ionic bonds. On the other hand, diluent compositions containing a large proportion of normal serum and relatively low concentrations of salt and detergent would be expected to be satisfactory diluents but not effective virus inactivators.

It was an object of the present invention to provide diluent solutions that could be used in preparing specimens for immunoassay analysis that would act effectively to inactivate any virus present while not reducing the specificity and sensitivity of the tests.

SUMMARY OF THE INVENTION

This invention relates to methods for inactivating viruses by diluting specimens with effective amounts of novel specimen inactivator media, particularly in preparing specimens for immunoassay analysis. This invention also relates to particular compositions of matter that serve both as diluents and inactivator media, which, in the course of preparing specimens for analysis, inactivate virus present. The methods and diluent compositions of the invention can be broadly used for inactivating viruses in specimens being prepared for immunoassay, including the inactivation of both HTLV-III and Hepatitis virus. Advantageously, viruses in the specimens are inactivated on dilution prior to analysis, thus eliminating the possibility of infection from discarded specimens, wash solutions and solid phase media. Unexpectedly, as an additional benefit of this invention, we found that immunoassays conducted on serum specimens diluted with the present inactivating compositions demonstrated improved specificity and sensitivity.

The inactivating composition of the invention is an immunoassay serum diluent that contains from 0.05 to 1% non-ionic surfactant in addition to the conventional serum, buffers and preservatives and has an ionic strength in the range of about 21 to about 35 mS/cm.

BRIEF DESCRIPTION OF THE DRAWINGS

Figure 1:
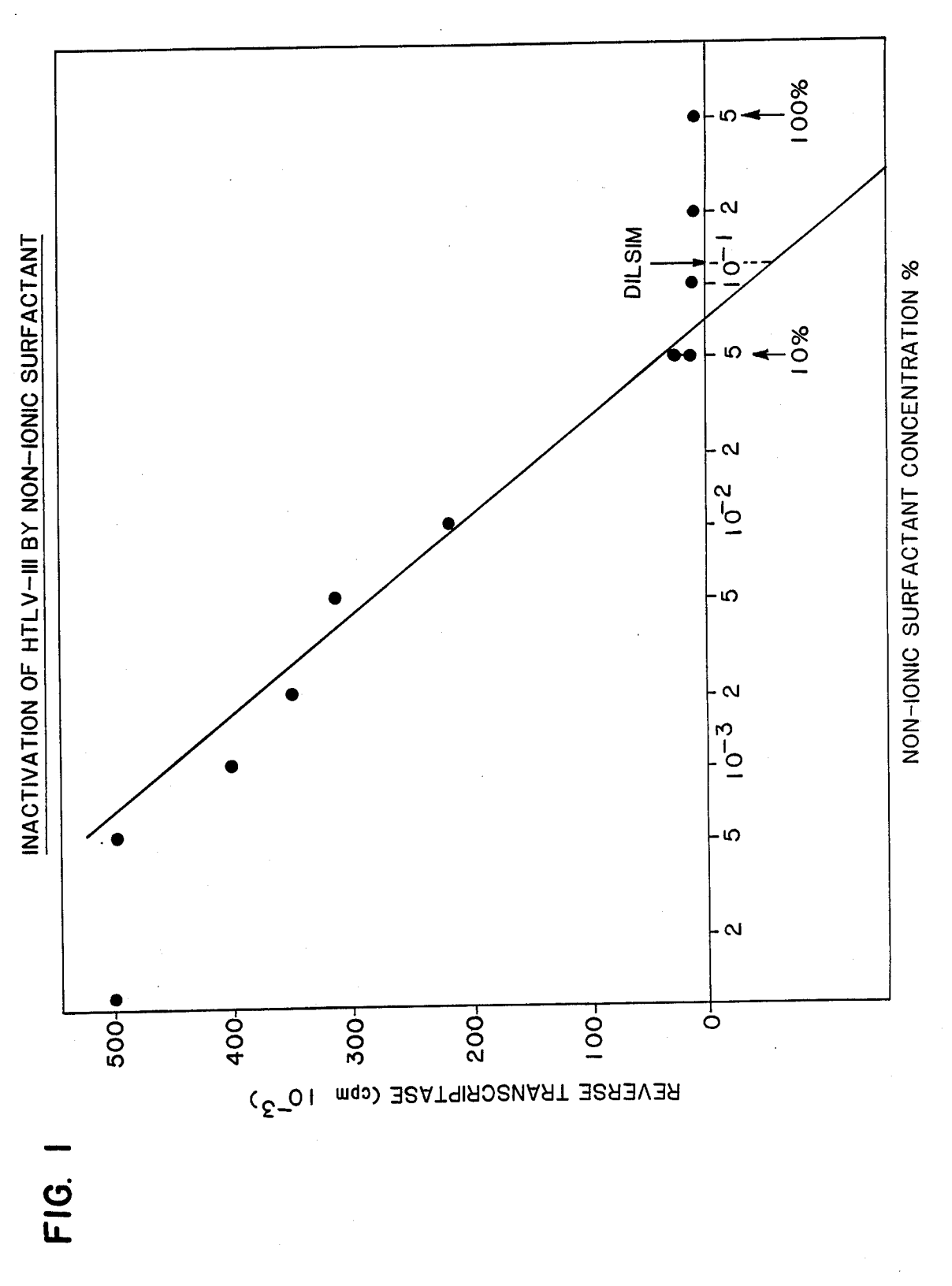

FIG. 1 shows the inactivation of HTLV-III by a non-ionic surfactant. The inactivation of the virus was tested using a reverse transcriptase assay for various concentrations of surfactant in water. [References 1 and 11 from Spire et al, *Lancet*, Oct. 20th, 1984.]

DETAILED DESCRIPTION OF THE EMBODIMENTS

Figure 2:
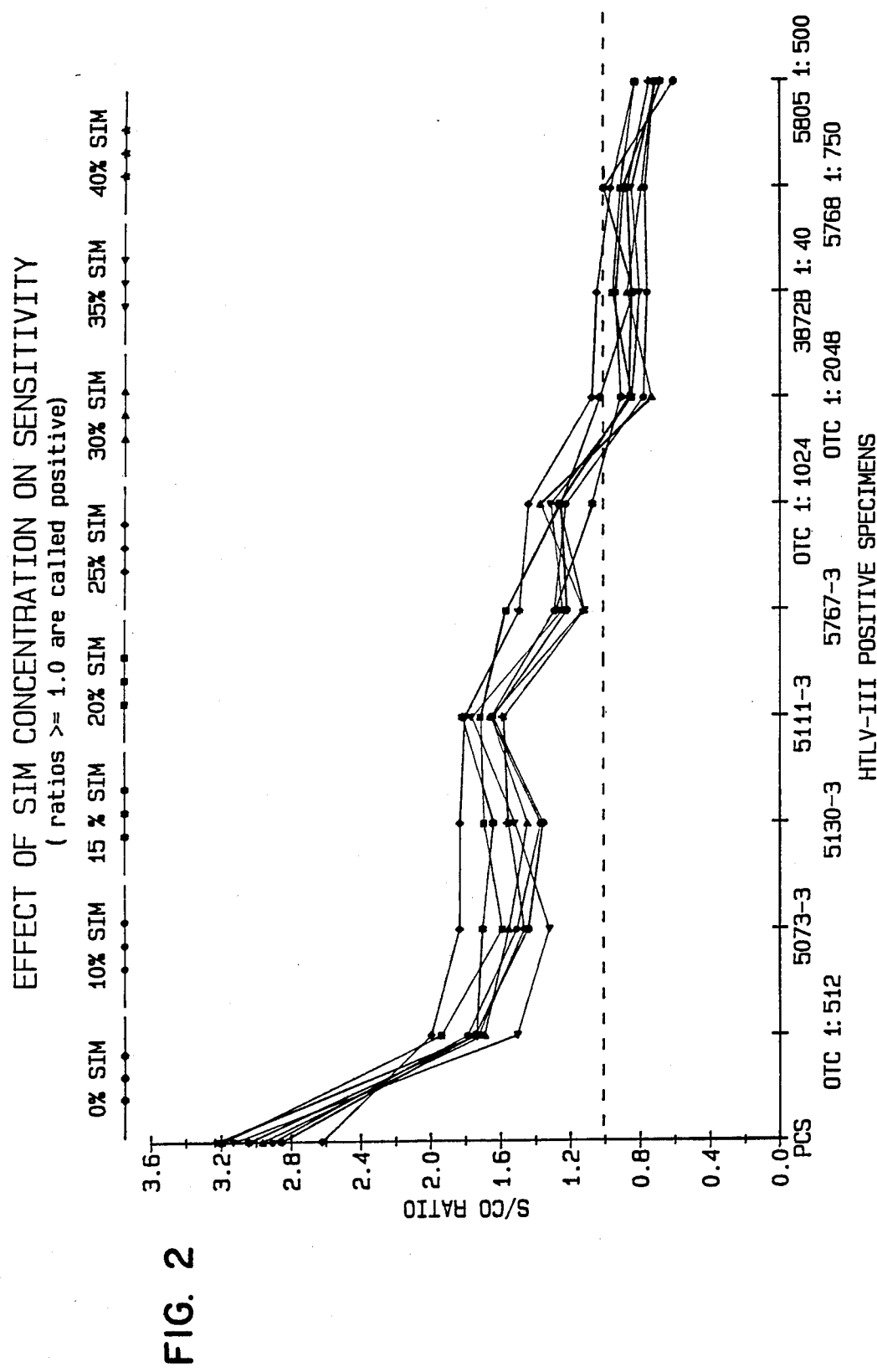
Figure 3:
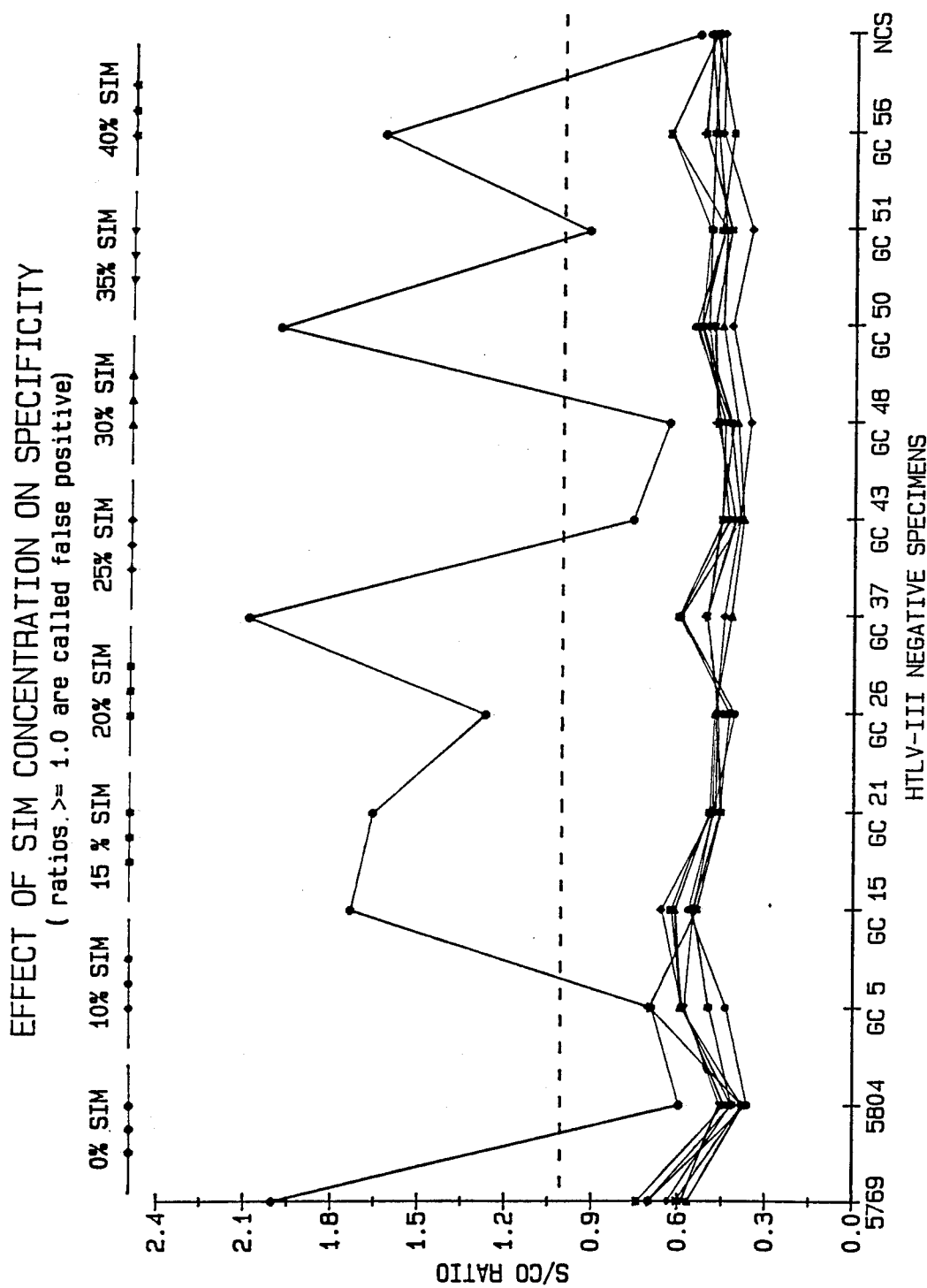

Conventional diluents for preparing specimens contain normal goat serum in phosphate buffered saline, a preservative (e.g., Thimerosal TM) and non-ionic surfactants (e.g., Tween-20 TM). In the discussion that follows, all percentage compositions are in weight percent. A typical composition comprises:

10% by weight normal goat serum;
0.85% by weight sodium chloride (0.15M);
0.125% by weight sodium phosphate, dibasic (0.0088M);
0.018% by weight sodium phosphate, monobasic monohydride (0.0012M); and
0.05% by weight Tween-20 TM.

In, for example, analyzing samples of blood products, it is essential to detect all specimens that are truly positive in order to prevent the transmission of virus-caused diseases such as AIDS and Hepatitis. It is also critical, however, to minimize false positives, thereby eliminating repeated testing and alarming the individuals from whom the specimens were obtained.

We have discovered that by increasing the sodium chloride and surfactant concentrations, the diluent will inactivate any virus present in the specimens. The novel inactivating diluents according to the invention contain at least 1% by weight sodium chloride, or an equivalent salt or salts to provide an ionic strength of at least about 21 mS/cm, and at least 0.05% by weight non-ionic surfactant (e.g., NP-40). Ionic strength is used to define and characterize the compositions of the invention, as salts other than NaCl can provide the same results. They have proven to be effective inactivators and have, unexpectedly and advantageously, improved both the sensitivity and specificity of the immunoassays. Useful compositions according to the invention have been found to have ionic strengths of from about 21 to about 35 mS/cm, and about 0.05 to 1% by weight non-ionic surfactant. Preferred compositions have from about 23 to about 30 mS/cm, and contain 0.05-1% non-ionic surfactant. The most preferred range of ionic strengths is about 24 to about 28 mS/cm, and best results, particularly regarding sensitivity, have been observed with diluents having an ionic strength of about 26 mS/cm. The other ingredients can vary more greatly without detracting from the composition of the invention.

Examples of useful compositions are as follows:
Specimen Inactivator Medium (SIM)
10% normal goat serum
1.08–3.66% NaCl (0.184–0.64M);
0.125% Na$_2$HPO$_4$;
0.018% NaH$_2$PO$_4$.H$_2$O; and
0.05–0.5% non-ionic surfactant (e.g., 0.0–0.05% Tween-20 TM and 0.05–0.5% NP-40).

A preferred embodiment of this composition, referred to below as dilute SIM (Dilsim-I) comprises:
10% normal goat serum
1.4% NaCl (0.24M);
0.125% Na$_2$HPO$_4$ (0.0088M);
0.018% NaH$_2$PO$_4$.H$_2$O (0.0012M); and
0.175% non-ionic surfactant (e.g., 0.05% Tween-20 TM and 0.125% NP-40).

The increased sensitivity and specificity achieved using the present inactivating diluents were enhanced by adding to the Dilsim-I composition small portions of nonfat dry milk and bovine serum albumin. Good results may be obtained by including, for example, from 0.05 to 0.5% non-fat dry milk and 0.02 to 0.5% bovine serum albumin. A preferred composition, referred to as Dilsim-II below, comprises:

10% normal goat serum
1.4% NaCl (0.24M);
0.125% Na$_2$HPO$_4$ (0.0088M);
0.018% NaH$_2$PO$_4$.H$_2$O (0.0012M);
0.125% non-ionic surfactant (e.g., 0.05% Tween-20 TM and 0.125% NP-40);
0.26% nonfat dry milk; and
0.13% bovine serum albumin.

Inactivating diluent compositions according to the invention may be used in preparing specimens for immunoassay whenever viruses may be present in order to eliminate the possibility that virus-caused diseases could be spread by contact with the test samples, wash solutions or solid media. The present diluent solutions can be used in preparing specimens for any antigen-antibody immunoassay tests. In fact, since this possibility is a likelihood for all test specimens in a serology lab, such diluent/virus inactivators should be included in most, if not all, antibody assay procedures, which amount to several million each year.

For the purpose of demonstrating the efficacy of the present inactivating diluents, immunoassays for the presence of HTLV-III antibodies in blood and blood product samples were conducted using HTLV-III antigenic material from disrupted virus preparations coated on Bio-EnzaBead TM plastic coated metallic beads. The HTLV-III virus was propagated in T-lymphocyte cultures (Popovic et al, *Science* 224: 497–500, 1984). The same principles, however, apply to any antibody-antigen immunoassays, particularly the enzyme-linked immunosorbent assays (ELISA), which are well known in the art (Saxinger et al, *Lab. Invest.* 49: 371–377, 1983).

The HTLV-III Bio-EnzaBead TM Test Kits provide rapid, sensitive and specific ELISA detection of HTLV-III antibody in human serum or plasma. Specimens nonreactive in the test may be considered negative for HTLV-III antibody. Specimens that test as reactive initially are retested in duplicate using the HTLV-III Bio-EnzaBead TM test. The specimens that are found to be repeatably reactive are considered to be positive for HTLV-III antibody, and these tests should be confirmed by another test such as the Western Blot technique (Sarngadharan et al, *Science* 224: 506–508, 1984).

The HTLV-III antigen used to coat the plastic covered metallic beads in the test was derived from HTLV-III virus propagated in T-lymphocyte culture (Popovic et al, supra). After mass propagation by cell culture techniques, the virus is purified by ultracentrifugation, the antigen further purified, and applied to plastic coated ferrous metal beads to be used as a solid phase in HTLV-III Bio-EnzaBead TM enzyme immunoassays. In the Bio-EnzaBead TM assay, the solid phase containing antigen is transferred from reaction mixtures and wash solutions in 96-well plates using a magnetic transfer device, which advantageously limits the quantity of specimens, reaction mixtures and wash solutions required. Other solid phase media can be substituted, such as antigen coated strips, although the quantities of reagents used and wastes produced will be greater.

Improved Immunoassay Specificity and Sensitivity

The advantageous properties of the novel diluent compositions were demonstrated using Bio-EnzaBead ™ tests. Individual HTLV-III antigen beads were incubated with serum or plasma specimens, binding any antibody to HTLV-III present in the specimens to antigens on the surface of the beads. After washing the beads free from unbound specimen material, they were incubated with goat anti-human immunoglobulins conjugated with horseradish peroxidase. The conjugate reacted with the human immunoglobulin that characterized the antibodies bound to antigens on the beads. The beads were then washed free of unbound enzyme conjugate and transferred to ABTS substrate (2,2'-azino-di[3-ethyl-benzthia-zolinesulfonate]) solution containing hydrogen peroxide. After incubation, a greenish color developed around each bead in proportion to the amount of antibody bound to that bead. The enzyme reaction was stopped by adding a fluoride solution, and the beads were swirled to evenly disperse the color in the well. The beads were then removed from each well and the color intensity of each well was measured in a 96-well ELISA plate reader, in which the absorbance values of controls and specimens were determined with a 690 nm wavelength reader. Specimens giving absorbance values equal to or greater than the designated cutoff value were considered to be reactive for HTLV-III antibody (HTLV-III Bio-EnzaBead ™, Qualitative Enzyme Immunoassay for the Detection of Antibody to HTLV-III in Human Serum or Plasma, Litton Bionetics, Inc., Mar. 29th, 1985). Substrates other than ABTS, e.g., OPD (orthophenylenediamine) and TMB (tetramethylbenzidine), and wavelengths other than 690 nm may be used just as well with the Dilsim solutions.

In conducting these tests, the specimens were diluted using the composition of the invention in the form of SIM, Dilsim-I or Dilsim-II. When specimen inactivator (SIM) was used, 10 µl of sample were diluted with 300 µl of SIM. To prepare the specimen for testing, 300 µl of diluted 1× diluent were added to 10 µl of the sample diluted with SIM, as above. 1× diluent comprises 10% normal goat serum, 0.86% NaCl, 0.125% $Na_2HPO_4$, 0.018% $NaH_2PO_4 \cdot H_2O$ and 0.05% surfactant in water.

To prepare Dilsim-I solution, 1 part SIM concentrate was diluted with 3 parts of 1× diluent. The resulting Dilsim-I solution was used to dilute the specimen in the ratio of 1 part specimen with 75 parts Dilsim-I (1:75).

Dilsim-II was prepared in the same way as Dilsim-I with 0.26 weight percent non-fat dry milk and 0.13 weight percent bovine serum albumin added.

Samples for testing according to the Bio-EnzaBead ™ procedure were prepared by making the appropriate dilution, as above, in the 96-well plates. One bead was then placed into each well containing control or specimen, and the beads were swirled to mix the specimens with inactivating diluent solutions. The plates of beads were then incubated for 90 to 100 minutes at 37±2° C., after which the beads were removed using a magnetic transfer device. The beads were then washed by manipulating them in and out of a separate 96-well plate containing wash solution, transferred into enzyme conjugate, swirled two or three times, and incubated for 30 to 35 minutes at 37±2° C. The beads were then removed using a magnetic transfer device and washed in two wash plates, after which they were placed in a plate containing ABTS substrate. The beads were then swirled and allowed to incubate without agitation, uncovered, at room temperature for 10 to 12 minutes. Stop solution (1.25% NaF) was then added to each well, the beads were swirled to disperse the color in each well and then removed using a magnetic transfer device. A 96-well ELISA plate reader was then used to determine the absorbance value for the color intensity in each well. The results were evaluated by comparing the absorbance value with the mean absorbance value for three negatives control serum wells. Samples having absorbance values greater than the cutoff value (mean plus delta) were scored as reactive. All reactive specimens were retested in duplicate to determine whether they were repeatedly reactive.

In Table I data showing optical density results for specimens diluted with 1× diluent, and various percentages of SIM in 1× diluent are reported. The column labeled "25% SIM" is the same composition as Dilsim-I. A confirmation of whether or not antibodies to HTLV-III were present in the specimen is indicated by the Western Blot results, for which those samples labeled "P" indicated the presence of HTLV-III antibodies. The results reported indicated that, in addition to inactivating the virus, the use of various concentrations of SIM in 1× diluent, from 10% through 75% SIM, resulted in more accurate determinations of the presence of HTLV-III antibodies in the specimens tested. Concentrations of 25% SIM (Dilsim-I) through 75% SIM eliminated all false positives. Specimens 14 and 16 suggest that SIM not be used in 100% concentrations, as the possibility of false negatives could occur. For these tests, all readings less than the cutoff value of 0.11 plus the mean for the three negative control serum wells were reported as negative. The ionic strength of these compositions was measured in units of mS/cm to be 21.2 for 10% SIM, 26.2 for 25% SIM, and 34.6 for 50% SIM.

Table II presents the results of comparative ELISA tests for HTLV-III performed on the same samples diluted with 1× diluent, Dilsim-I and Dilsim-II on V2 (chromatographically purified virus lysate) Bio-EnzaBeads ™, and Dilsim-II on V1 (virus lysate) Bio-EnzaBeads ™. The results in these tests were evaluated using Western Blot analyses as the standard. It may be observed, however, that in samples having absorbance cutoff values close to the standard mean + delta for showing a minimum positive result, the Bio-EnzaBead ™ tests may even provide better resolution than some Western Blot tests (e.g., Tests 14, 18, 21, 22, 23 and 30).

The unexpected advantages of improved sensitivity and selectivity using diluents according to the invention were demonstrated in Tests 13, 14, 18, 32, 34, 35, 39, 40, 45, 46, 49, 50 and 52, in which conventional diluents (1×) reported false positives, while Dilsim-I and Dilsim-II correctly indicated negative results. In addition, many tests demonstrated better resolution being the present diluents (e.g., Samples 42, 47, 48 and 51). The additional advantage of using the Dilsim-II composition, containing non-fat dry milk and bovine serum albumin, can be observed, as increased specificity is obtained. For example, false positives obtained using either the 1× diluent or Dilsim-I became unequivocal negatives, which were confirmed by Western Blot analysis (e.g., Tests 31, 33 and especially 36). The better resolution obtained by Dilsim-II over Dilsim-I was further demonstrated in other examples (e.g., Tests 18, 22, 41-44, 47 and 52).

Table III provides additional results illustrating the sensitivity and specificity obtained using the SIM diluent at different concentrations (0%, 10%, 15%, 20%, 30%, and 40% SIM) in a Dilsim II diluent composition. The ionic strength of each solution in millisemens per centimeter (mS/cm) ($\pm 2\%$) measured using a CDM 83 conductivity meter (Radiometer A/S, Copenhagen) is also given. The same results are presented in FIGS. II and III. Serum specimens OTC 1:512 through 5130-3 are HTLV-III antibody positive, and 5769 through GC 56 are HTLV-III antibody negative. The positive samples are diluted in the ratio indicated (e.g., the OTC specimen is diluted one part sample to 512 parts diluent in OTC 1:512, and the 5130 specimen comprises a $10^{-3}$ fraction of the diluted sample in 5130-3).

In FIG. II an S/CO (the ratio of mean optical density to cut off optical density ratio) of 1.0 is used as the limit aft or above which the sample is determined to be positive. The more dilute samples (OTC 1:2048, 3872B 1:40, 5768 1:750, and 5805 1:500) illustrate that the 25% SIM diluent composition (ionic strength about 26.2 mS/cm) provides the greatest sensitivity for weakly positive and highly dilute samples. It also illustrates that false negatives can be avoided by adopting a safety margin of, for example, an S/CO ratio of 0.8.

FIG. III confirms the showing in Table I, that the SIM diluent in most any proportion effectively eliminates false positive results.

TABLE I

| | | Effective Range of Decreasing SIM | | | | | |
|---|---|---|---|---|---|---|---|
| | | | Optical Densities at 690 nm | | | | |
| Specimen No. | Western Blot | 1x Diluent | 10% SIM | 25% SIM | 50% SIM | 75% SIM | 100% SIM |
| Mean of 3 Negative Controls | | .096 | .091 | .092 | .127 | .085 | .094 |
| Cutoff Value (Mean + 0.11) | | .206 | .201 | .202 | .254 | .195 | .204 |
| Positive Control (1) | P | .516 | .451 | .443 | .468 | .443 | .408 |
| 2 | P | .454 | .486 | .466 | .435 | .401 | .403 |
| 3 | — | .139 | .123 | .126 | .105 | .120 | .073 |
| 4 | P | .142 | .095 | .126 | .100 | .105 | .080 |
| 5 | — | .120 | .100 | .148 | .092 | .092 | .066 |
| 6 | P | .503 | .440 | .460 | .369 | .349 | .292 |
| 7 | P | .171 | .162 | .174 | .165 | .159 | .105 |
| 8 | P | .298 | .329 | .340 | .300 | .235 | .244 |
| 9 | P | .367 | .351 | .411 | .403 | .318 | .262 |
| 10 | — | .102 | .097 | .113 | .112 | .097 | .092 |
| 11 | P | .436 | .319 | .346 | .279 | .379 | .360 |
| 12 | P | .132 | .135 | .164 | .138 | .129 | .105 |
| 13 | — | .118 | .103 | .103 | .103 | .100 | .073 |
| 14 | P | .311 | .287 | .264 | .224 | .224** | .140** |
| 15 | — | .116 | .082 | .108 | .085 | .085 | .042 |
| 16 | P | .332 | .295 | .260 | .275 | .211 | .088** |
| 17 | P | .471 | .489 | .394 | .453 | .409 | .291 |
| 18 | P | .557 | .508 | .477 | .483 | .442 | .436 |
| 19 | P | .604 | .604 | .572 | .557 | .459 | .522 |
| 20 | — | .113 | .105 | .098 | .105 | .085 | .070 |
| 21 | — | .105 | .098 | .140 | .098 | .068 | .075 |
| 22 | — | .070 | .082 | .070 | .078 | .058 | .063 |
| 23 | — | .169 | .121 | .172 | .127 | .125 | .118 |
| 24 | P | .485 | .489 | .479 | .379 | .325 | .350 |
| 25 | P | .479 | .459 | .374 | .384 | .325 | .311 |
| 26 | — | .125 | .073 | .090 | .085 | .078 | .070 |
| 27 | P | .388 | .337 | .388 | .388 | .321 | .299 |
| 28 | — | .141 | .132 | .122 | .143 | .120 | .158 |
| 29 | — | .239* | .129 | .112 | .170 | .141 | .118 |
| 30 | — | .090 | .087 | .082 | .095 | .082 | .095 |
| 31 | — | .087 | .090 | .080 | .075 | .061 | .078 |
| 32 | P | .481 | .388 | .286 | .374 | .219 | .319 |
| 33 | P | .485 | .442 | .429 | .291 | .309 | .267 |
| 34 | — | .225* | .121 | .112 | .140 | .109 | .105 |
| 35 | P | .437 | .458 | .442 | .268 | .362 | .254 |
| 36 | — | .323* | .243 | .164 | .143 | .161 | .151 |
| 37 | — | .223* | .178 | .133 | .166 | .158 | .166 |
| 38 | — | .263* | .178 | .120 | .137 | .125 | .123 |
| 39 | — | .155 | .131 | .123 | .131 | .105 | .140 |
| 40 | — | .332* | .154 | .105 | .126 | .144 | .163 |
| 41 | — | .226* | .169 | .110 | .145 | .107 | .183 |
| 42 | — | .362* | .239* | .164 | .209 | .158 | .174 |
| 43 | — | .243* | .174 | .141 | .157 | .182 | .174 |
| 44 | — | .303* | .145 | .136 | .163 | .131 | .134 |

*False Positive
**False Negative

TABLE II

ELISA Tests for HTLV-III

| Test Number | 1x Diluent V2 Beads 690 nm O.D. | Delta | Dilsim I V2 Beads 690 nm O.D. | Delta | Dilsim II V2 Beads 690 nm O.D. | Delta | Dilsim II V1 Beads 690 nm O.D. | Delta | Western Blot Reactivity NCI[1] | BRI[2] | Other |
|---|---|---|---|---|---|---|---|---|---|---|---|
| Mean of Negative Controls | .111 | | .081 | | .092 | | .089 | | | | |
| Cutoff Value (Mean + 0.11) | .221 | | .191 | | .202 | | .199 | | | | |
| 1 | .494 | .383 | .505 | .424 | .517 | .425 | .595 | .506 | | + | |
| 2 | .148 | .037 | .139 | .058 | .141 | .049 | .138 | .049 | | (+)[3] | |
| 3 | .099 | −.012 | .082 | .001 | .079 | −.013 | .074 | −.015 | | (−) | |
| 4 | .302 | .191 | .333 | .252 | .285 | .193 | .334 | .245 | | (+) | |
| 5 | .398 | .287 | .442 | .361 | .422 | .330 | .438 | .349 | | (+) | |
| 6 | .298 | .178 | .412 | .331 | .371 | .279 | .416 | .327 | | (+) | |
| 7 | .139 | .028 | .130 | .049 | .100 | .008 | .118 | .029 | | (+) | |
| 8 | .248 | .137 | .321 | .240 | .255 | .163 | .298 | .209 | | (+) | |
| 9 | .083 | −.028 | .075 | −.006 | .075 | −.017 | .073 | −.016 | | (−)[3] | |
| 10 | .174 | .063 | .214 | .133 | .249 | .157 | .268 | .179 | | (+) | |
| 11 | .108 | −.003 | .110 | .029 | .119 | .027 | .145 | .056 | − | − | |
| 12 | .517 | .406 | .497 | .416 | .391 | .299 | .574 | .485 | + | + | |
| 13 | .277 | .166 | .180 | .099 | .211 | .119 | .177 | .088 | − | − | |
| 14 | .220 | .109 | .167 | .086 | .136 | .044 | .176 | .087 | − | + | |
| 15 | .197 | .086 | .197 | .116 | .181 | .089 | .295 | .206 | − | − | |
| 16 | .584 | .473 | .511 | .430 | .528 | .436 | .570 | .481 | + | + | |
| 17 | .124 | .013 | .130 | .049 | .112 | .020 | .135 | .046 | + | + | |
| 18 | .250 | .139 | .147 | .066 | .098 | .006 | .103 | .014 | − | vw[4]− | |
| 19 | .144 | .033 | .126 | .045 | .108 | .016 | — | — | − | − | |
| 20 | .099 | −.012 | .090 | .009 | .085 | −.007 | .095 | .006 | − | − | |
| 21 | .118 | .007 | .096 | .015 | .096 | .004 | .096 | .007 | − | vw + | |
| 22 | .162 | .051 | .119 | .038 | .085 | −.007 | .098 | .009 | − | w[5]+ | |
| 23 | .097 | −.014 | .085 | .004 | .093 | .001 | .088 | −.001 | − | vw[4]+ | |
| 24 | .169 | .058 | .095 | .014 | .089 | −.003 | .087 | −.002 | − | − | |
| 25 | .460 | .349 | .463 | .382 | .447 | .355 | .468 | .379 | + | + | |
| 26 | .103 | −.008 | .108 | .027 | .169 | .077 | .144 | .055 | + | w[5]+ | |
| 27 | .118 | .007 | .114 | .033 | .120 | .028 | .125 | .036 | + | w + | |
| 28 | .141 | .030 | .101 | .020 | .104 | .012 | .105 | .016 | − | − | |
| 29 | .328 | .217 | .427 | .346 | .480 | .388 | .446 | .357 | + | + | |
| 30 | .124 | .013 | .105 | .024 | .125 | .033 | .123 | .034 | − | vw + | |
| 31 | .290 | .179 | .245 | .164 | .088 | −.004 | .079 | .010 | | | |
| 32 | .297 | .186 | .154 | .073 | .081 | −.011 | .084 | −.005 | | | |
| 33 | .285 | .174 | .202 | .121 | .101 | .009 | .093 | .004 | | | |
| 34 | .337 | .226 | .148 | .067 | .105 | .013 | .085 | −.004 | | | |
| 35 | .245 | .134 | .183 | .102 | .094 | .002 | .088 | −.001 | | | |
| 36 | .537 | .426 | .402 | .321 | .108 | .016 | .111 | .022 | | | |
| 37 | .178 | .067 | .149 | .068 | .182 | .090 | .169 | .080 | + | | |
| 38 | .105 | −.006 | .126 | .045 | .070 | −.022 | .068 | −.021 | − | | |
| 39 | .282 | .171 | .086 | .005 | .075 | −.017 | .081 | −.008 | | | − |
| 40 | .321 | .210 | .080 | −.001 | .079 | −.013 | .083 | −.006 | | | − |
| 41 | .145 | .034 | .112 | .031 | .078 | −.014 | .080 | −.009 | | | − |
| 42 | .190 | .079 | .122 | .041 | .076 | −.016 | .071 | −.018 | | | − |
| 43 | .132 | .021 | .110 | .029 | .081 | −.011 | .088 | −.001 | | | − |
| 44 | .117 | .006 | .114 | .033 | .086 | −.006 | .086 | −.003 | | | − |
| 45 | .273 | .162 | .076 | −.005 | .078 | −.014 | .071 | −.018 | | | − |
| 46 | .288 | .177 | .083 | .002 | .079 | −.013 | .077 | −.012 | | | − |
| 47 | .171 | .060 | .115 | .034 | .086 | −.006 | .084 | −.005 | | | − |
| 48 | .196 | .085 | .083 | .002 | .081 | −.011 | .075 | −.014 | | | − |
| 49 | .404 | .293 | .093 | .012 | .090 | −.002 | .088 | −.001 | | | − |
| 50 | .230 | .119 | .085 | .004 | .076 | −.016 | .077 | −.012 | | | − |
| 51 | .167 | .056 | .091 | .010 | .078 | −.014 | .087 | −.001 | | | − |
| 52 | .257 | .140 | .134 | .053 | .088 | −.004 | .100 | .011 | | | − |

[1]National Cancer Institute
[2]Bionetics Research, Inc.
[3]( ): Expected Western Blot Reactivity
[4]vw: Very Weak
[5]w: Weak

TABLE III

| SAMPLE | 10% SIM MEAN OD | CV | DELTA | S/CO | INT. | 30% SIM MEAN OD | CV | DELTA | S/CO | INT. | SAMPLE |
|---|---|---|---|---|---|---|---|---|---|---|---|
| OTC 1:512 | 0.397 | 1.2% | 0.285 | 1.786 | + | 0.359 | 19.1% | 0.257 | 1.691 | + | OTC 1:512 |
| OTC 1:1024 | 0.271 | 4.7% | 0.159 | 1.221 | + | 0.291 | 0.7% | 0.189 | 1.370 | + | OTC 1:1024 |
| OTC 1:2048 | 0.173 | 2.0% | 0.061 | 0.777 | − | 0.156 | 22.3% | 0.054 | 0.733 | − | OTC 1:2048 |
| 3872B 1:40 | 0.168 | 3.8% | 0.056 | 0.755 | − | 0.185 | 14.5% | 0.083 | 0.873 | + − | 3872B 1:40 |
| 5767-3 | 0.286 | 2.0% | 0.174 | 1.288 | + | 0.238 | 8.3% | 0.136 | 1.123 | + | 5767-3 |
| 5768 1:750 | 0.171 | 9.9% | 0.059 | 0.770 | − | 0.168 | 1.3% | 0.066 | 0.790 | − | 5768 1:750 |

TABLE III-continued

| SAMPLE | MEAN OD | CV | DELTA | S/CO | INT. | MEAN OD | CV | DELTA | S/CO | INT. | SAMPLE |
|---|---|---|---|---|---|---|---|---|---|---|---|
| 5805 1:500 | 0.158 | 3.6% | 0.046 | 0.712 | − | 0.153 | 0.5% | 0.051 | 0.719 | − | 5805 1:500 |
| 5073-3 | 0.334 | 2.5% | 0.222 | 1.505 | + | 0.329 | 6.9% | 0.227 | 1.552 | + | 5073-3 |
| 5111-3 | 0.368 | 9.4% | 0.256 | 1.655 | + | 0.351 | 15.7% | 0.249 | 1.656 | + | 5111-3 |
| 5130-3 | 0.304 | 11.2% | 0.192 | 1.369 | + | 0.307 | 1.2% | 0.205 | 1.446 | + | 5130-3 |
| 5769 | 0.156 | 2.3% | 0.044 | 0.700 | − | 0.120 | 16.0% | 0.018 | 0.564 | − | 5769 |
| 5804 | 0.080 | 3.5% | −0.032 | 0.360 | − | 0.080 | 4.4% | −0.022 | 0.375 | − | 5804 |
| SC 5 | 0.097 | 5.1% | −0.016 | 0.435 | − | 0.125 | 4.5% | 0.023 | 0.590 | − | GC 5 |
| GC 15 | 0.126 | 6.2% | 0.013 | 0.565 | − | 0.130 | 6.0% | 0.028 | 0.611 | − | GC 15 |
| GC 21 | 0.107 | 6.0% | −0.006 | 0.480 | − | 0.104 | 8.2% | 0.002 | 0.491 | − | GC 21 |
| GC 26 | 0.091 | 0.8% | −0.022 | 0.408 | − | 0.101 | 19.6% | −0.001 | 0.476 | − | GC 26 |
| GC 37 | 0.132 | 0.0% | 0.020 | 0.595 | − | 0.093 | 9.1% | −0.009 | 0.419 | − | GC 37 |
| GC 43 | 0.087 | 2.5% | −0.025 | 0.390 | − | 0.084 | 6.7% | −0.018 | 0.378 | − | GC 43 |
| GC 48 | 0.095 | 8.9% | −0.017 | 0.428 | − | 0.089 | 6.4% | −0.013 | 0.401 | − | GC 48 |
| GC 50 | 0.122 | 8.1% | 0.010 | 0.550 | − | 0.101 | 3.5% | −0.001 | 0.453 | − | GC 50 |
| GC 51 | 0.099 | 3.6% | −0.013 | 0.444 | − | 0.098 | 10.1% | −0.004 | 0.441 | − | GC 51 |
| GC 56 | 0.106 | 13.3% | −0.006 | 0.477 | − | 0.142 | 54.5% | 0.040 | 0.637 | − | GC 56 |
| PCS | 0.645 | — | 0.533 | 2.905 | + | 0.658 | — | 0.556 | 2.964 | + | PCS |
| NCS MEAN | 0.112 | 36.0% | | | | 0.102 | 35.2% | | | | |
| CUTOFF | 0.222 | | | | | 0.212 | | | | | |
| aS/ca | 21.2 | | | | | 28.0 | | | | | |

| | 15% SIM | | | | | 35% SIM | | | | | |
|---|---|---|---|---|---|---|---|---|---|---|---|
| SAMPLE | MEAN OD | CV | DELTA | S/CO | INT. | MEAN OD | CV | DELTA | S/CO | INT. | SAMPLE |
| OTC 1:512 | 0.360 | 14.5% | 0.262 | 1.734 | + | 0.317 | 17.8% | 0.216 | 1.502 | + | OTC 1:512 |
| OTC 1:1024 | 0.222 | 0.0% | 0.124 | 1.069 | + | 0.277 | 10.5% | 0.176 | 1.310 | + | OTC 1:1024 |
| OTC 1:2048 | 0.188 | 5.3% | 0.090 | 0.905 | +− | 0.178 | ERR | 0.077 | 0.844 | +− | OTC 1:2048 |
| 3872B 1:40 | 0.195 | 5.1% | 0.097 | 0.939 | +− | 0.169 | 5.5% | 0.068 | 0.799 | − | 3872B 1:40 |
| 5767-3 | 0.266 | 10.9% | 0.168 | 1.278 | + | 0.262 | 0.0% | 0.161 | 1.242 | + | 5767-3 |
| 5768 1:750 | 0.185 | 10.3% | 0.087 | 0.888 | +− | 0.179 | 2.4% | 0.078 | 0.848 | +− | 5768 1:750 |
| 5805 1:500 | 0.142 | 21.9% | 0.044 | 0.684 | − | 0.149 | 5.2% | 0.048 | 0.704 | − | 5805 1:500 |
| 5073-3 | 0.353 | 0.4% | 0.255 | 1.700 | + | 0.279 | 27.7% | 0.178 | 1.320 | + | 5073-3 |
| 5111-3 | 0.378 | 4.3% | 0.280 | 1.818 | + | 0.373 | 7.0% | 0.272 | 1.765 | + | 5111-3 |
| 5130-3 | 0.341 | 7.3% | 0.243 | 1.640 | + | 0.321 | 8.2% | 0.220 | 1.519 | + | 5130-3 |
| 5769 | 0.145 | 1.0% | 0.047 | 0.698 | − | 0.124 | 6.8% | 0.023 | 0.588 | − | 5769 |
| 5804 | 0.086 | 9.1% | −0.012 | 0.412 | − | 0.096 | 10.3% | −0.005 | 0.455 | − | 5804 |
| GC 5 | 0.103 | 18.6% | 0.005 | 0.494 | − | 0.122 | 1.2% | 0.021 | 0.578 | − | GC 5 |
| GC 15 | 0.115 | 3.1% | 0.017 | 0.551 | − | 0.116 | 4.3% | 0.015 | 0.547 | − | GC 15 |
| GC 21 | 0.095 | 3.0% | −0.003 | 0.457 | − | 0.102 | 9.1% | 0.001 | 0.481 | − | GC 21 |
| GC 26 | 0.089 | 4.0% | −0.009 | 0.426 | − | 0.098 | 7.2% | −0.003 | 0.464 | − | GC 26 |
| GC 37 | 0.125 | 5.1% | 0.027 | 0.600 | − | 0.105 | 5.4% | 0.004 | 0.506 | − | GC 37 |
| GC 43 | 0.090 | 7.1% | −0.008 | 0.431 | − | 0.095 | 9.7% | −0.006 | 0.455 | − | GC 43 |
| GC 48 | 0.096 | 5.9% | −0.002 | 0.462 | − | 0.093 | 3.8% | −0.008 | 0.445 | − | GC 48 |
| GC 50 | 0.105 | 3.4% | 0.007 | 0.503 | − | 0.110 | 16.7% | 0.009 | 0.530 | − | GC 50 |
| GC 51 | 0.103 | 10.3% | 0.005 | 0.494 | − | 0.104 | 4.8% | 0.003 | 0.498 | − | GC 51 |
| GC 56 | 0.101 | 21.0% | 0.003 | 0.486 | − | 0.133 | 48.6% | 0.032 | 0.638 | − | GC 56 |
| PCS | 0.632 | — | 0.534 | 3.043 | + | 0.650 | — | 0.549 | 3.130 | + | PCS |
| NCS MEAN | 0.098 | 18.6% | | | | 0.101 | 34.3% | | | | |
| CUTOFF | 0.208 | | | | | 0.211 | | | | | |
| aS/ca | 23.0 | | | | | 29.6 | | | | | |

| | 20% SIM | | | | | 40% SIM | | | | | |
|---|---|---|---|---|---|---|---|---|---|---|---|
| SAMPLE | MEAN OD | CV | DELTA | S/CO | INT. | MEAN OD | CV | DELTA | S/CO | INT. | SAMPLE |
| OTC 1:512 | 0.405 | 9.8% | 0.305 | 1.932 | + | 0.376 | 6.0% | 0.268 | 1.725 | + | OTC 1:512 |
| OTC 1:1024 | 0.264 | 16.9% | 0.164 | 1.257 | + | 0.276 | 1.5% | 0.168 | 1.266 | + | OTC 1:1024 |
| OTC 1:2048 | 0.177 | 10.4% | 0.077 | 0.844 | +− | 0.188 | 12.4% | 0.080 | 0.860 | +− | OTC 1:2048 |
| 3872B 1:40 | 0.200 | 0.7% | 0.100 | 0.954 | +− | 0.184 | ERR | 0.076 | 0.844 | +− | 3872B 1:40 |
| 5767-3 | 0.328 | 4.7% | 0.228 | 1.564 | + | 0.244 | 28.7% | 0.136 | 1.117 | + | 5767-3 |
| 5768 1:750 | 0.190 | 12.7% | 0.090 | 0.906 | +− | 0.190 | 6.0% | 0.082 | 0.872 | +− | 5768 1:750 |
| 5805 1:500 | 0.173 | 15.5% | 0.073 | 0.825 | +− | 0.163 | 6.5% | 0.055 | 0.745 | − | 5805 1:500 |
| 5073-3 | 0.333 | 6.8% | 0.233 | 1.588 | + | 0.319 | 0.0% | 0.211 | 1.463 | + | 5073-3 |
| 5111-3 | 0.359 | 1.2% | 0.259 | 1.712 | + | 0.345 | 2.0% | 0.237 | 1.583 | + | 5111-3 |
| 5130-3 | 0.355 | 3.2% | 0.255 | 1.693 | + | 0.340 | 3.5% | 0.232 | 1.557 | + | 5130-3 |
| 5769 | 0.155 | 20.1% | 0.055 | 0.739 | − | 0.133 | 1.6% | 0.025 | 0.608 | − | 5769 |
| 5804 | 0.092 | 2.3% | −0.008 | 0.436 | − | 0.083 | 4.3% | −0.025 | 0.378 | − | 5804 |
| GC 5 | 0.123 | 26.0% | 0.023 | 0.584 | − | 0.153 | 6.0% | 0.045 | 0.700 | − | GC 5 |
| GC 15 | 0.131 | 2.2% | 0.031 | 0.625 | − | 0.117 | 18.1% | 0.009 | 0.537 | − | GC 15 |
| GC 21 | 0.104 | 4.8% | 0.004 | 0.494 | − | 0.100 | 9.2% | −0.008 | 0.456 | − | GC 21 |
| GC 26 | 0.093 | 11.5% | −0.007 | 0.441 | − | 0.103 | 7.6% | −0.005 | 0.470 | − | GC 26 |
| GC 37 | 0.127 | 6.1% | 0.027 | 0.603 | − | 0.107 | 0.7% | −0.002 | 0.508 | − | GC 37 |
| GC 43 | 0.096 | 3.7% | −0.004 | 0.455 | − | 0.086 | 9.9% | −0.022 | 0.410 | − | GC 43 |
| GC 48 | 0.089 | 10.4% | −0.011 | 0.422 | − | 0.100 | 7.8% | −0.008 | 0.475 | − | GC 48 |
| GC 50 | 0.111 | 10.9% | 0.011 | 0.527 | − | 0.102 | 3.5% | −0.006 | 0.484 | − | GC 50 |
| GC 51 | 0.097 | 9.5% | −0.003 | 0.460 | − | 0.090 | 4.0% | −0.019 | 0.427 | − | GC 51 |
| GC 56 | 0.088 | 3.2% | −0.012 | 0.420 | − | 0.109 | 37.6% | 0.001 | 0.520 | − | GC 56 |
| PCS | 0.669 | — | 0.569 | 3.191 | + | 0.677 | — | 0.569 | 3.229 | + | PCS |
| NCS MEAN | 0.100 | 23.2% | | | | 0.108 | 39.0% | | | | |
| CUTOFF | 0.210 | | | | | 0.218 | | | | | |
| aS/ca | 24.4 | | | | | 31.0 | | | | | |

| | 0% SIM | | | | | 25% SIM | | | | | |
|---|---|---|---|---|---|---|---|---|---|---|---|
| SAMPLE | MEAN OD | CV | DELTA | S/CO | INT. | MEAN OD | CV | DELTA | S/CO | INT. | SAMPLE |
| OTC 1:512 | 0.416 | 0.0% | 0.288 | 1.744 | + | 0.400 | 1.2% | 0.309 | 1.991 | + | OTC 1:512 |

TABLE III-continued

| | | | | | | | | | | | |
|---|---|---|---|---|---|---|---|---|---|---|---|
| OTC 1:1024 | 0.299 | 0.7% | 0.170 | 1.252 | + | 0.288 | 7.4% | 0.197 | 1.435 | + | OTC 1:1024 |
| OTC 1:2048 | 0.245 | 1.4% | 0.116 | 1.025 | + | 0.215 | 3.3% | 0.124 | 1.071 | + | OTC 1:2048 |
| 3872B 1:40 | 0.199 | 13.5% | 0.071 | 0.834 | +− | 0.209 | 4.7% | 0.118 | 1.042 | + | 3872B 1:40 |
| 5767-3 | 0.290 | 7.3% | 0.162 | 1.216 | + | 0.299 | 3.6% | 0.208 | 1.488 | + | 5767-3 |
| 5768 1:750 | 0.240 | 9.4% | 0.112 | 1.006 | + | 0.193 | 16.9% | 0.102 | 0.962 | +− | 5768 1:750 |
| 5805 1:500 | 0.145 | 6.8% | 0.017 | 0.608 | − | 0.166 | 7.3% | 0.075 | 0.825 | +− | 5805 1:500 |
| 5073-3 | 0.344 | 5.1% | 0.215 | 1.440 | + | 0.368 | 4.0% | 0.277 | 1.831 | + | 5073-3 |
| 5111-3 | 0.392 | 7.6% | 0.264 | 1.644 | + | 0.362 | 7.2% | 0.271 | 1.801 | + | 5111-3 |
| 5130-3 | 0.324 | 3.7% | 0.195 | 1.356 | + | 0.367 | 6.2% | 0.276 | 1.829 | + | 5130-3 |
| 5769 | 0.478 | 1.6% | 0.349 | 2.002 | + | 0.127 | 2.2% | 0.036 | 0.633 | − | 5769 |
| 5804 | 0.142 | 11.0% | 0.014 | 0.595 | − | 0.083 | 3.4% | −0.008 | 0.414 | − | 5804 |
| GC 5 | 0.165 | 4.3% | 0.037 | 0.692 | − | 0.118 | 1.8% | 0.027 | 0.586 | − | GC 5 |
| GC 15 | 0.413 | 6.8% | 0.285 | 1.732 | + | 0.132 | 4.3% | 0.041 | 0.658 | − | GC 15 |
| GC 21 | 0.395 | 11.8% | 0.267 | 1.656 | + | 0.097 | 2.9% | 0.006 | 0.483 | − | GC 21 |
| GC 26 | 0.303 | 18.5% | 0.174 | 1.268 | + | 0.095 | 3.7% | 0.004 | 0.471 | − | GC 26 |
| GC 37 | 0.498 | 4.8% | 0.370 | 2.088 | + | 0.106 | 9.3% | 0.015 | 0.444 | − | GC 37 |
| GC 43 | 0.182 | 35.5% | 0.053 | 0.761 | − | 0.094 | 2.3% | 0.003 | 0.392 | − | GC 43 |
| GC 48 | 0.152 | 8.4% | 0.023 | 0.637 | − | 0.085 | 1.7% | −0.006 | 0.356 | − | GC 48 |
| GC 50 | 0.473 | 14.1% | 0.345 | 1.983 | + | 0.101 | 7.7% | 0.010 | 0.421 | − | GC 50 |
| GC 51 | 0.219 | 6.8% | 0.090 | 0.916 | +− | 0.085 | 0.8% | −0.006 | 0.354 | − | GC 51 |
| GC 56 | 0.388 | 3.8% | 0.259 | 1.625 | + | 0.110 | 25.2% | 0.019 | 0.459 | − | GC 56 |
| PCS | 0.681 | 5.0% | 0.553 | 2.855 | + | 0.625 | — | 0.534 | 2.621 | + | PCS |
| NCS MEAN | 0.129 | 2.8% | | | | 0.091 | 36.7% | | | | |
| CUTOFF | 0.239 | | | | | 0.201 | | | | | |
| aS/ca | 17.2 | | | | | 26.2 | | | | | |

EXAMPLES

Inactivation of HTLV-III

The inactivation of viruses using Dilsim-I and Dilsim-II was evaluated in tests that measured the efficacy of these diluents for inactivating HTLV-III in human specimens. The results obtained demonstrate that Dilsim-I reduced the infection titer of HTLV-III more than $10^4$, which was the detection limit of the experiment, and Dilsim-II reduced the titer of HTLV-III at least $10^3$ or to an undetectable level at the dilution tested. The following examples illustrate the efficacy of both Dilsim-I and Dilsim-II in inactivating HTLV-III in human serum specimens.

Example 1—Toxicity Study

Before initiating the infectivity assays, it was important to determine the concentration of Dilsim-I that could be used with cell cultures without toxic effect. An experiment was carried out using two types of target cells: (a) normal peripheral blood mononuclear cells (NPB) and (b) a clone of Jurkett T-cell line (D6).

Materials and Methods

A. Target Cells
Normal peripheral blood mononuclear cells (NPB)
Clone of Jurkett T-cell line (D6)
B. Diluent: Dilsim-I
C. Each of the target cells were treated 48 hours with 5 $\mu$g/ml phytohemagglutinin (PHA-P) in growth media; cells were washed and infected with virus treated with the indicated concentration of Dilsim-I.
D. Cell cultures were grown in growth media [NPB 10% T-cell growth factor (TCGF), 20% fetal bovine serum (FBS) RPMI 1640; D6 10% FBS RPMI 1640] and monitored for 2 weeks for overall growth and appearance.

Results:

| | Effect on Cell | |
|---|---|---|
| Dilsim-I Dilutions | NPB | D6 |
| 1:10 | Toxic | Toxic |
| 1:100 | Toxic | Toxic |
| 1:200 | Toxic | Toxic |
| 1:300 | Slight Effect | Slight Effect |
| 1:1000 | No Effect | No Effect |
| Control | Normal | Normal |

Conclusion:

At dilution of 1:300 or greater, Dilsim-I is not toxic to NPB cells or to D6 cells.

Example 2—Dilsim-I Effect on Virus Infectivity

Materials and Methods

A.
Starting virus concentration [$10^4$X]
Target cell—D6
Diluent: Dilsim-I
B. Treated Virus
1. 0.002 ml of HTLV-III/H9 [$10^4$X] was incubated with 0.15 ml of Dilsim-I (1X) and incubated at 37° C. for 0, 1, 5, or 10 minutes.
2. Following incubation, samples were diluted to 45 ml (1:300 dilution) with serum-free media, resulting in a virus dilution of $1/(2.25 \times 10^4)$. This was used to infect $4 \times 10^6$ D6 target cells (pretreated for 20 minutes with 20 $\mu$g/ml DEAE-dextran), for 1 hour at 37° C. Quadruplicate cultures were carried for each time point. Each culture was checked for infectivity at 8 days, 23 days, and 27 days post-infection.
C. Positive Virus Control
HTLV-III/H9 was diluted with seven serial 10-fold dilutions [$1/(5 \times 10^2)$ to $1/(5 \times 10^8)$] in a 1/300 dilution of Dilsim-I; 1 ml of each dilution level was used to infect $4 \times 10^6$ D6 cells (37° C., 60 min). Quadruplicate cultures were carried for each dilution. Each culture was checked for infectivity at 13 days and 21 days post-infection.

Results:
A. Treated Virus
Dilution of treated virus used to infect target cells was $1/(2.25 \times 10^4)$.

|                    | Time of Exposure (min) | | | |
|--------------------|---|---|---|---|
|                    | 0 | 1 | 5 | 10 |
| Days Post Infection |   | (#pos/#tested) | | |
| 8                  | 1/4 | 0/4 | 0/4 | 0/4 |
| 23                 | 4/4 | 0/4 | 0/4 | 0/4 |
| 27                 | 4/4 | 0/4 | 0/4 | 0/4 |
| Conclusion         | 4/4 | 0/4 | 0/4 | 0/4 |

B. Positive Virus Control

|                    | Virus Dilution [$1/(5 \times 10^y)$] | | | | | | |
|--------------------|---|---|---|---|---|---|---|
|                    | y = 2 | y = 3 | y = 4 | y = 5 | y = 6 | y = 7 | y = 8 |
| Days Post Infection |   |   | (#pos/#tested) | | | | |
| 13                 | 4/4 | 4/4 | 4/4 | 4/4 | 4/4 | 4/4 | 4/4 |
| 21                 |     | 4/4 | 4/4 | 4/4 | 4/4 | 4/4 | 4/4 |

Conclusions:

A dilution of treated virus of $1/(2.25 \times 10^4)$ was used to "infect" target cells. The HTLV-III used had a titer of greater than $1/(5 \times 10^8)$. These data indicate that at exposure times equal to or greater than one minute, Dilsim-I reduced the infection titer of HTLV-III more than $10^4$ TCID$_{50}$ units (dose level lethal to 50% of virus), or to an undetectable level at the dilutions tested.

Example 3—Dilsim-II Effect on Virus Infectivity

Materials and Methods

A. Virus: HTLV-III/H9 (100X concentration)
Cells: Normal peripheral blood mononuclear cells (NPB), treated 48 hours with 5 µg/ml PHA-P; rinsed and grown in RPMI-1640 with 20% FBS, 10% IL-2. 1X Diluent; 20 ml diluent concentrate (1:5)+1.0 ml (5% Tween 20) (1:100)+79 ml H$_2$O.
Dilsim-II (1X); powdered Dilsim-II dissolved in 60 ml 1X diluent.

B. Treatment of Virus with Dilsim-II 0.01 ml virus was mixed with 0.1 ml Dilsim-II and incubated for 0, 1, 5, 10 minutes. Samples were then diluted to 30 ml in media and 1 ml each used to infect $6 \times 10^6$ NPB. Following infection, triplicate cultures were carried for each time point. Each culture was checked for infectivity at 5 days, 9 days, 12 days, 16 days, and 19 days post-infection.

C. Treatment of Virus with Diluent 1X.
(Same set up as B.)

D. Positive virus control in 1/300 Dilsim-II.
HTLV-III diluted in Dilsim-II at a 1/300 dilution. Six serial 10-fold dilutions were used to infect NPB ($1/10^3$ to $1/10^8$).

E. Positive virus control in 1/300 Diluent.
HTLV-III diluted in diluent at a 1/300 dilution. Dilutions used to infect NPB = $1/10^5$ to $1/10^8$.

Summary of Results

1. Dilsim-II treated virus  Virus dilution assayed = 1/10  Virus dilution used to infect cells $1/(3 \times 10^3) = (3.3 \times 10^{-4})$

|                    | Time of Exposure (min) | | | |
|--------------------|---|---|---|---|
|                    | 0 | 1 | 5 | 10 |
| Days Post Infection |   | (#pos/#tested) | | |
| 5                  | 0/3 | 0/3 | 0/3 | 0/3 |
| 9                  | 0/3 | 0/3 | 0/3 | 0/3 |
| 12                 | 0/3 | 0/3 | 0/3 | 0/3 |
| 16                 | 1/3 | 0/3 | 0/3 | 0/3 |
| 19                 | 1/3 | 0/3 | 0/3 | 0/3 |
| Conclusion         | 1/3 | 0/3 | 0/3 | 0/3 |

2. Diluent Treated Virus
Virus dilution treated 1/10
Virus dilution used for infection $1/(3 \times 10^3) = (3.3 \times 10^{-4})$

|                    | Time of Exposure (min) | | | |
|--------------------|---|---|---|---|
|                    | 0 | 1 | 5 | 10 |
| Days Post Infection |   | (#pos/#tested) | | |
| 5                  | 3/3 | 1/3 | 0/3 | 0/3 |
| 9                  | 3/3 | 3/3 | 0/3 | — |
| 12                 | 3/3 | 3/3 | 1/3 | 3/3 |
| 16                 | 3/3 | 3/3 | 2/3 | 3/3 |
| 19                 | 3/3 | 3/3 | 3/3 | 3/3 |
| Conclusion         | 3/3 | 3/3 | 3/3 | 3/3 |

The embodiments presented above and the examples set forth herein are provided to illustrate the invention, but not for purposes of limitation. The invention is intended to include all equivalents and modifications within the skill of the art encompassed by the appended claims.

We claim:

1. A virus inactivating diluent composition for preparing specimens for immunoassay, comprising a salt and a surfactant in amounts effective for inactivating viruses in said specimens without reducing the accuracy of the immunoassay, wherein the diluent composition has an ionic strength of from about 21 to about 35 mS/cm and a surfactant concentration of from about 0.05 to about 1% by weight, wherein the salt is an inorganic salt having an anion selected from Cl$^-$ or an anion of essentially equal or smaller molecular weight, and wherein the surfactant is a non-ionic surfactant.

2. The diluent composition of claim 1, comprising normal goat serum and sodium phosphate.

3. The diluent composition of claim 2, comprising about 0.05 to about 0.5% of the non-ionic surfactant.

4. The diluent composition of claim 3, comprising about 10% by weight normal goat serum.

5. The diluent composition of claim 2, comprising nonfat dry milk and bovine serum albumin.

6. The diluent composition of claim 5, comprising from about 0.1 to about 1% by weight nonfat dry milk and from about 0.1 to about 1% by weight bovine serum albumin.

7. The diluent composition of claim 6, comprising about 0.05 to about 0.5% of the non-ionic surfactant.

8. In a method for conducting immunoassay tests for the presence of antibodies to a virus in a specimen, an improvement comprising diluting the specimen with the diluent of claim 1, whereby virus in the specimen is inactivated and the specificity and sensitivity of the immunoassay is improved.

9. The method of claim 8, wherein the virus is Human T-Lymphotropic Virus.

10. The method of claim 8, wherein the virus is Hepatitis virus.

11. In a method for conducting immunoassay tests for the presence of a virus in a specimen, an improvement comprising diluting the specimen with the diluent of claim 1, whereby any Human T-Lymphotropic Virus in the specimen is inactivated and the specificity and sensitivity of the immunoassay test is improved.

12. The diluent composition of claim 1, having an ionic strength of from about 21 to about 31 mS/cm.

13. The diluent composition of claim 1, having an ionic strength of from about 23 to about 30 mS/cm.

14. The diluent composition of claim 1, having an ionic strength of from about 24 to about 28 mS/cm.

15. The diluent composition of claim 1, having an ionic strength of about 26 mS/cm.

16. The diluent composition of claim 1, comprising about 0.1 to about 0.5% non-ionic surfactant.

17. The method of claim 8, wherein the diluent comprises nonfat dry milk.

18. The method of claim 11, wherein the diluent comprises nonfat dry milk.

19. The diluent composition of claim 1, wherein the non-ionic surfactant is a condensate of ethylene oxide with aromatic alcohols.

* * * * *